(12) United States Patent
Shimizu et al.

(10) Patent No.: US 7,534,582 B2
(45) Date of Patent: *May 19, 2009

(54) METHOD FOR MEASURING THE AMOUNT OF NATRIURETIC PEPTIDES IN A SAMPLE

(75) Inventors: Hiroyuki Shimizu, Settsu (JP); Hidehisa Asada, Osaka-fu (JP); Kazuaki Endo, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/785,394

(22) Filed: Apr. 17, 2007

(65) Prior Publication Data

US 2007/0196888 A1 Aug. 23, 2007

Related U.S. Application Data

(63) Continuation of application No. 09/530,013, filed as application No. PCT/JP98/01470 on Mar. 31, 1998, now Pat. No. 7,226,729.

(30) Foreign Application Priority Data

Oct. 24, 1997 (JP) .............................. 1997-292982

(51) Int. Cl.
*C12Q 1/37* (2006.01)
(52) U.S. Cl. .............................. 435/24; 435/4; 435/69.2
(58) Field of Classification Search .................. 435/24, 435/4, 69.2
See application file for complete search history.

(56) References Cited

U.S. PATENT DOCUMENTS 5,057,495 A 10/1991 Flynn et al.

FOREIGN PATENT DOCUMENTS

| EP | 0 393 640 B1 | 10/1990 |
|---|---|---|
| EP | 0 401 006 B1 | 12/1990 |
| EP | 0 709 678 B1 | 5/1996 |
| WO | WO-93/24531 | 12/1993 |

OTHER PUBLICATIONS

Nelesen R. et al. Plasma Atrial Natriuretic Peptide is Unstable Under Most Storage Conditions. Circulation vol. 86, pp. 463-466, 1992.*
Davidson N. et al. N-Terminal Proatrial Natriuretic Peptide and Brain Natriuretic Peptide are Stable for Up to 6 Hours in Whole Blood in vitro. Circulation 91(4)1276-7, 1995.*
Clin. Chem, vol. 42, No. 10, pp. 1627-1633 (1996).
Biochemical and Biophysical Research Communications, vol. 161, No. 3, pp. 1177-1183 (1989).
Pharmacology & Tocicology, vol. 68, No. 4, pp. 276-281 (1991).
P.J. Hunt et al., Biochem. Biophys. Res. Commun., 214 (3) : 1175-1183 (1995).
Nelesen et al.; Plasma Atrial Natriuretic Peptide is Unstable Under Most Storage Conditions; Circulation, vol. 86, No. 2; Aug. 1992; pp. 463-466.
Davidson et al.; Circulation, vol. 91, No. 4; Feb. 15, 1995; pp. 1276-1277.
Tsuji et al.; "Stability of human atrial natriuretic peptide in blood samples"; Clinica Chimica Act, 225; 1994; pp. 171-177.
Omland et al.; "Plasma Brain Natriuretic Peptide as an Indicator of Left Ventricular Systolic Function and Long-term Survival After Acute Myocardial Infarction"; Circulation, vol. 93, No. 11; Jun. 1, 1996; pp. 1963-1969.
Van der Kamp et al.; "Contact activation during incubation of five different polyurethanes or glass in plasma"; J Biomed Mater, Res.; Oct. 29, 1995; 1303-1306.
Ballermann; "A highly sensitive radioreceptor assay for atrial natriuretic peptide in rat plasma"; Am. J. Phys. 254:1; pp. F159-F163.
Costar: Corning Microplate selection guide, published Nov. 30, 2005, pp. 3 and 6.
Greiner: current catalogue 2005/2006 section 2, HTS Microplates, pp. 2, 6, 10.

* cited by examiner

*Primary Examiner*—Ralph Gitomer
(74) *Attorney, Agent, or Firm*—Birch, Stewart, Kolasch & Birch, LLP.

(57) ABSTRACT

A method for accurately measuring an amount of natriuretic peptides in a sample that has stood for at least 24 hours, in a plastic tube or a tube coated with silicone. This method makes it possible to measure natriuretic peptides stably and conveniently. Also provided is a method for measuring the amount of natriuretic acid in a sample at the time of collection by measuring the amount of natriuretic peptide in a blood sample at two periods of time after collection.

18 Claims, 3 Drawing Sheets

METHOD FOR MEASURING THE AMOUNT OF NATRIURETIC PEPTIDES IN A SAMPLE

CROSS-REFERENCE TO RELATED APPLICATIONS

The present application is a 37 C. F. R. § 1.53(b) continuation of U.S. application Ser. No. 09/530,013 filed Apr. 24, 2000, issued as U.S. Pat No. 7,226,729 on Jun. 5, 2007, which in turn claims priority to International Application No. PCT/JP98/01470 which has an International filing date of Mar. 31, 1998 and to Japanese Application No. 292982/1997 filed Oct. 24, 1997. The entire contents of each of these applications is hereby incorporated by reference.

TECHNICAL FIELD

This invention relates to methods for inhibiting the degradation of natriuretic peptides by using a container which comprises a material inhibiting the activation of a substance degrading the peptides and also relates to methods for measuring, assaying, collecting, and storing of the peptides by using the container.

BACKGROUND ART

A natriuretic peptide family consists of at least three types of natriuretic peptides, atrial natriuretic peptide (ANP), brain natriuretic peptide (BNP) and C type natriuretic peptide (CNP). CNP is a vascular proliferation-regulating peptide mainly secreted from endotherial cells. ANP and BNP are cardiac hormones mainly synthesized in and secreted from heart. These peptides are synthesized as pro-hormones and cleaved to be mature peptides, $\alpha$-ANP, $\alpha$-BNP, $\alpha$-CNP respectively. Human $\alpha$-ANP, $\alpha$-BNP, and $\alpha$-CNP consist of 28, 32, and 22 amino acid residues, respectively.

Some diseases cause the secretion of these natriuretic peptides into blood stream. Since the synthesis and secretion of ANP and BNP are promoted mainly by a load against atria and ventricles of heart, respectively, their secretions reflect changes of heart functions. Each peptide is used as a diagnostic indicator of heart diseases, especially heart failure. Measurement of both $\alpha$-ANP and $\alpha$-BNP by immunoassay has already been applied in the clinical field.

Since $\alpha$-ANP and $\alpha$-BNP are easily degraded by proteases in blood after the collection, they are extremely unstable in blood samples. Thus results of measurement had been greatly affected by the collecting methods, storing methods of specimens and the period from collection to measurement. To measure the concentration of the peptides exactly, addition of degradation inhibiting agents, e.g., aprotinin etc. or keeping specimens at low temperature had been essential. But, these handlings were complicate, required too many tasks, and not completed methods as pretreatment of specimens.

DISCLOSURE OF INVENTION

It is speculated that after blood collection natriuretic peptides are degraded by substances such as proteases in blood. To date, some protease inhibitors were added into the samples for the inhibition of the degradation of natriuretic peptides. But, it could not completely inhibit the degradation. The present inventors have speculated that coagulation factors activated by negatively charged solid phase such as glass surface accelerate the degradation of natriuretic peptides when specimens are collected into a container made of glass. The inventors have collected specimens by using a glass container wherein the face coming into contact with a specimen was coated with silicone, and obtained a result that the degradation of natriuretic peptides were inhibited.

The inventors have found out that the degradation of nartiuretic peptides by a substance such as proteases can be suppressed significantly by using a container coated with silicone upon measurement of natriuretic peptide.

The inventors have also found out that the degradation of natriuretic peptides can be suppressed by using a container made of plastic such as polyethylene terephthalate (PET), polystyrene, polypropylene, polyethylene and acrylic resin.

These results suggest that the degradation of natriuretic peptides in specimens can be suppressed by using a container wherein the face coming into contact with specimens is made of a material inhibiting the activation of a substance degrading the peptides upon handling specimens containing mammalian natriuretic peptides. Therefore, it is expected that the former complicated handling of specimens can be eliminated by using a container wherein the face coming into contact with specimens is made of materials other than glass upon the measurement of natriuretic peptides. Further expected is that these convenient specimens collecting methods for sample preparation give more exact results for diagnosis of heart diseases than conventional methods already used in the clinical field.

This invention is based on the results of the measurement of natriuretic peptides by thus established methods for the inhibition of degradation of mammalian natriuretic peptides by using a container which do not activate substances degrading the peptides in handling specimens containing the peptides.

This invention relates to a method for inhibiting the degradation of mammalian natriuretic peptides by using a container wherein the face coming into contact with specimens made of a materials, preferably, silicone or plastic, which inhibits the activation of the substances degrading the peptides.

Mammalian natriuretic peptides comprise at least ANP and BNP and precursors and derivatives of each peptide because in body there are not only the mature types but also the precursors such as $\gamma$-ANP and $\gamma$-BNP (BBRC, 214(3), (1995)), and their derivatives. Mammal means all kinds of mammal having natriuretic peptides, such as human, dog, pig, rat and mouse.

"Handling of specimens" means any kinds of handling for specimens, such as collection, storage, analysis, measurement and so on of the specimens.

"Materials inhibiting the activation of a substance degrading peptides" mean materials, which can inhibit the activation of substances degrading the peptides, such as proteases etc., and can at least form the face coming into contact with the specimen contained in a specimen collecting container. Examples of the material include silicone and plastic, preferably polyethylene, polyethylene terephthalate, polystyrene, polypropylene, polyamide, acrylic resin and so on. SILICONIZE L-25 (Ficon Co.) is given for example as commercially available silicone. It is possible for persons skilled in the art to coat usually used containers made of glass and polyethylene with silicone by using this reagent.

"Container" means all kinds of containers for specimen collection, storage, measurement and so on, for example, a container which is made of or coated with a material inhibiting the dagradation, preferably, with silicone or plastic.

Any kind of biological samples can be used for measuring specimens, and preferred is whole blood or blood plasma.

This invention relates to a measurement of natriuretic peptide in specimens which do not contain aprotinin.

Although aprotinin has been added into specimens to inhibit the degradation of natriuretic peptides by proteases which are already active in blood or are activated after blood collection, it can not inactivate them contained in biological samples completely.

This invention relates to a measuring method of mammalian natriuretic peptides which comprises the method for inhibiting the degradation of the peptides.

The measurement of natriuretic peptides can be carried out by a biological activity measurement, liquid chromatography, immunoassay and so on. The immunoassay can be performed, which may be competitive immunoassay or sandwich immunoassay, by persons skilled in the art. Otherwise, commercially available α-ANP assay kit "SHIONORIA ANP" (Shionogi & Co., Ltd.) or α-BNP assay kit "SHIONORIA BNP" (Shionogi & Co., Ltd.) can also be used for the measurement.

Furthermore, this invention relates to a kit for measuring mammalian natriuretic peptides. The kit comprises the method for inhibiting the degradation of the peptides in a specimen by using a container wherein the face coming into contact with the specimen is made of a material inhibiting the activation of a substance degrading the peptides upon the specimen collection or measurement.

EXAMPLE

More detail of this invention is explained in the following examples, which does not limit this invention.

Example 1

Measurement of BNP Using Glass Tubes (1) Preparation of silicone coated glass tubes: Commercially available glass tubes (Terumo, Tokyo, Japan) were washed with purified water once, and with 3% (V/V) silicone solution (SILICONIZE L-25: Ficon Co.,) three times. They were washed once again with purified water and dried for 90 min at 300° C.

(2) Preparation of a specimen for measurement: Venous blood from normal subject was collected into a blood-collecting tube containing EDTA (1.5 mg/ml EDTA.2Na). Human α-BNP (Peptide Institute, Osaka, Japan) was added to the collected blood to make its final concentration 200 pg/ml, to prepare a specimen.

(3) BNP measurement by IRMA method: The specimen was pippetted into the silicone-coated tubes and the non-coated tubes, respectively. They were allowed to stand for 0, 2, 6, and 24 hours at room temperature (25° C.). Blood cells were separated from these specimens by a centrifugation (Kokusan: H-107GA), ×2000 g, for 5 min at 4° C. These specimens were stored at −80° C. BNP immunoreactivities were measured by SHIONORIA BNP (Shionogi).

Briefly, 100 μl of plasma or standard solution (α-BNP solutions: 0, 4, 10, 150, 600, and 2000 pg/ml), were pippetted into Shionogi tubes (made of polystyrene: Shionogi), respectively. Two hundreds μl of iodine labeled anti-BNP antibody solution and a anti-BNP antibody immobilized polystyrene bead were added into the tubes. The mixture was stirred and then left alone for 18 hours at 4° C. After washing twice with 2 ml of washing solution, the radioactivities were measured by γ-counter ARC-600 (Aloka). The result is shown in FIG. 1.

In the case of using non-coated glass tubes (FIG. 1, ■), the ratio of residual BNP activity was about 20% after 24 hours-standing. On the other hand, the residual BNP activity ratio was about 80% even after 24 hours-standing and the activity of substances degrading peptides was suppressed by using the silicone-coated glass tubes (FIG. 1, □).

Figure 1:
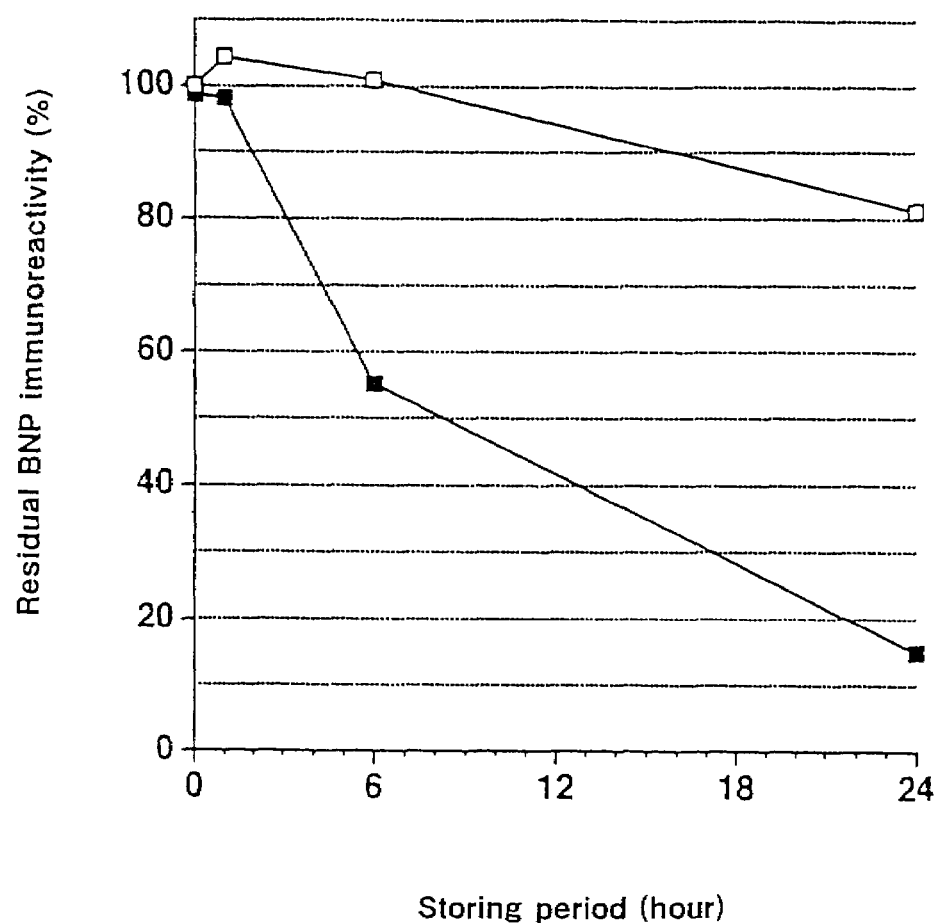
FIG. 1 shows the relationship between the storing periods in glass tubes or silicone-coated glass tubes at 25° C. and the residual activities of BNP like substances measured by various kinds of BNP measuring methods.

FIG. 1 shows that the activity of substances degrading natriuretic peptides can be suppressed by silicone-coating the face coming into contact with the specimen in a specimen collecting container.

Example 2

Measurement of BNP Using Polyethylene Terephthalate (PET) Tubes (1) Preparation of silicone-coated PET tubes: Commercially available PET tubes (Terumo, Tokyo, Japan) were washed with purified water once, and with 3% (V/V) silicone solution (SILICONIZE L-25: Ficon Co.) three times. They were washed once again with purified water and dried.

(2) Preparation of a specimen for measurement: Fifty ml of venous blood from normal subject was collected into a blood-collecting tubes containing EDTA (1.5 mg/ml EDTA.2Na). Human α-BNP (Peptide Institute) was added to the collected blood to make its final concentration 200 pg/ml, to prepare a specimen.

(3) BNP measurement by IRMA method: The specimen was pippetted into the silicone-coated PET tubes, the silicone-coated glass tubes, the non-coated PET tubes and the non-coated glass tubes, respectively. They were allowed to stand for 0, 2, 6, 24, and 72 hours at room temperature (25° C.). Blood cells were separated from these specimens by a centrifugation (Kokusan: H-107GA), ×2000 g, for 5 min at 4° C. These specimens were stored at −80° C. BNP immunoreactivities in these blood plasma were measured by SHIONORIA BNP (Shionogi). The measurement was performed by the same method as that described in Example 1.

Figure 2:
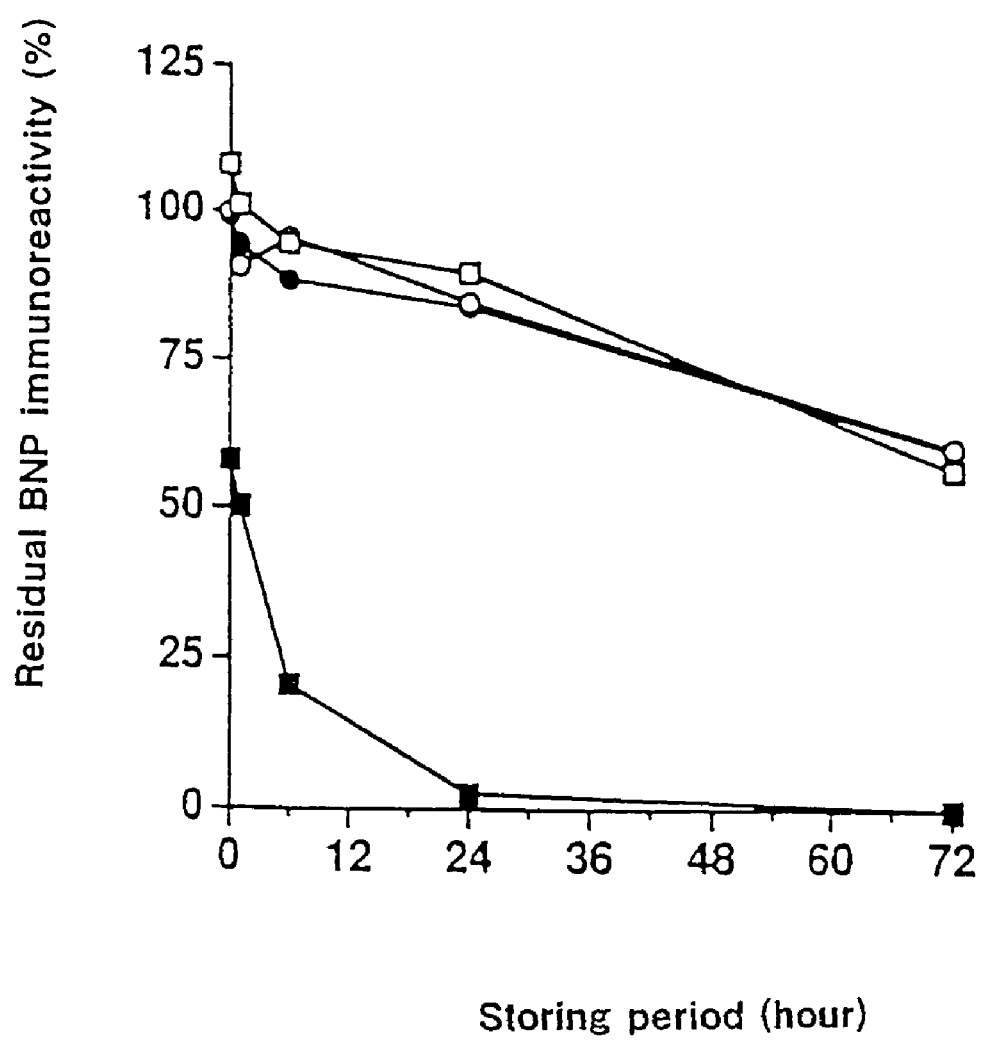
FIG. 2 shows the relationship between the storing periods in silicone-coated or non-coated polyethylene terephthalate tubes or glass tubes at 25° C. and the residual activities of BNP like substances.

The result is shown in FIG. 2. The ratio of residual BNP activity was about 80% after 24 hours-standing due to the suppression of the activity of substances degrading peptides by using the silicone-coated PET tubes (FIG. 2, ○) and the non-coated PET tubes (FIG. 2, ●). The result was the same as that of using the silicone-coated glass tubes (FIG. 2, □). On the other hand, the ratio of residual BNP activity was 0% after 24 hours-standing by using the non silicone-coated glass tubes (FIG. 2, ■).

Example 3

Measurement of BNP Using Plastic Tubes

As specimen storing containers, glass tubes, silicone coated glass tubes, and plastic tubes were used. Five kinds of plastic tubes, i.e., polystyrene tubes, polypropylene A tubes, polypropylene B tubes, reinforced polyethylene tubes, and acrylic resin tubes were used.

(1) BNP Measurement by IRMA Method

The specimen was pippetteed into each of the above described plastic tubes, coated with or without silicone. They were allowed to stand for 0, and 24 hours at room temperature (25° C.). Blood cells were separated from these specimens by a centrifugation (Kokusan: H-107GA), ×2000 g, for 5 min at 4° C. The obtained plasma specimens were stored at −80° C. BNP immunoreactivities in these plasma specimens were measured by SHIONORIA BNP (Shionogi). The measurement was performed by the same method as Example 1.

Figure 3:
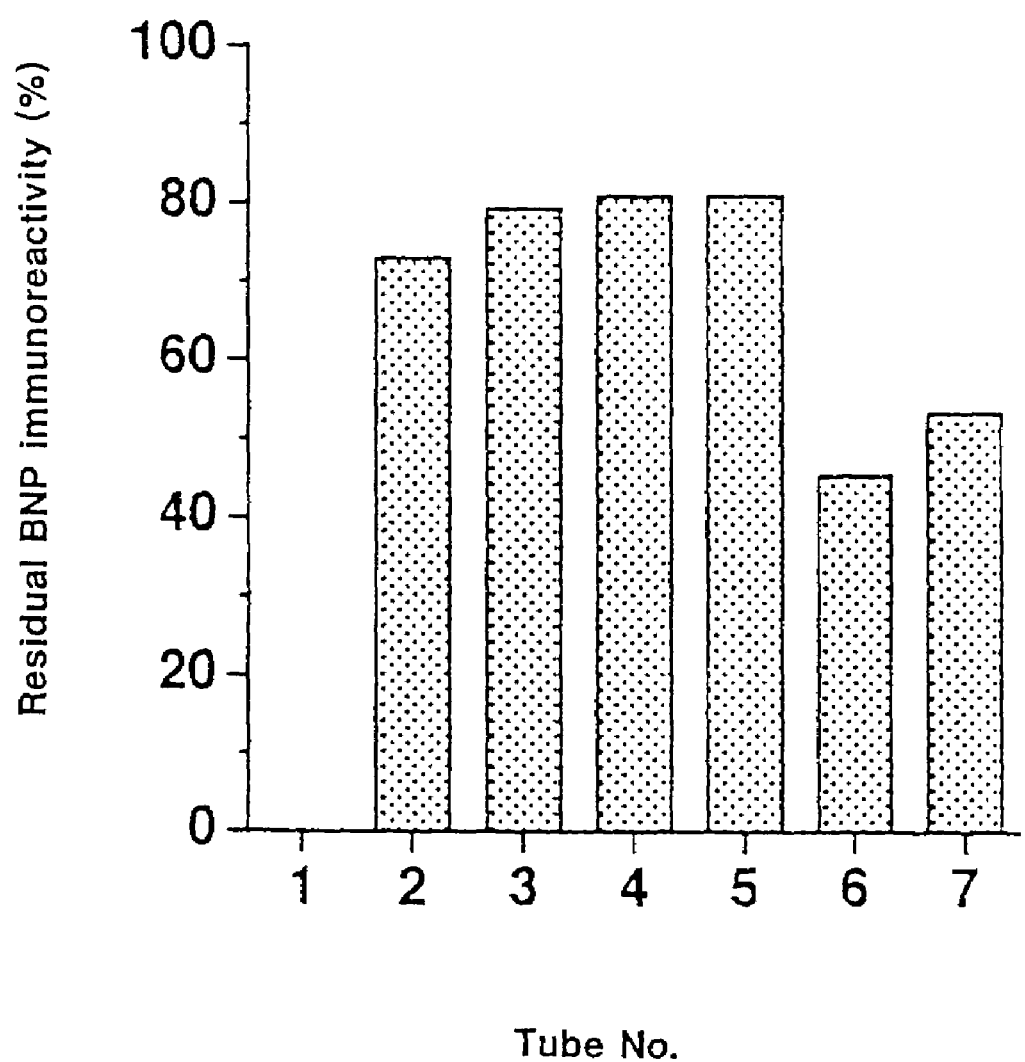
FIG. 3 shows the residual BNP activities of BNP like substances stored in silicone-coated or non-coated glass tube and various kinds of plastic tubes, such as polystyrene, polypropylene, reinforced polyethylene and acrylic resin for 24 hours at 25° C.

The ratios of the residual BNP activities were 50% or more due to the suppression of the activity of substances degrading peptides by using any kinds of plastic tube used, i.e., polystyrene tube, polypropylene A tube, polypropylene B tube, reinforced polyethylene tube, and acrylic resin tube (FIG. 3, lane 3, 4, 5, 6, and 7). The result was the same as that by using the silicone-coated glass tube (FIG. 3, lane 2). On the other hand, the ratio of residual BNP activity was 0% by using the non-coated glass tube (FIG. 3, lane 1).

The residual activity of BNP remarkably decreased in glass tubes because BNP was degraded by substances degrading the peptides such as proteases.

Conversely, the decrease of the residual BNP activity was suppressed in silicone-coated glass tubes. Furthermore, in plastic tubes made of polyethylene terephthalate, polystyrene, polypropylene, polyethylene or acrylic resin coated with or without silicone, the degradation of BNP was suppressed due to the inhibition of the activation of substances degrading peptides.

EFFECT OF INVENTION

The method of this invention for inhibiting the peptide degradation by using a container wherein the face coming into contact with a specimen is made of a materials inhibiting the activation of the degrading substances, provides stable and dependable clinical data on which collecting methods, storing methods and period till measurement do not have any effects.

Further, it will contribute to an exact diagnosis of heart disease by providing economical, convenient stable and dependable clinical data because blood samples can be used for measuring without complicate handling.

What is claimed is:

1. A method for measuring an amount of a natriuretic peptide in a biological sample after at least 24 hours comprising: measuring by a standard method the amount of the natriuretic peptide in said sample that has stood at a temperature of 4° C. to room temperature for at least 24 hours in a plastic tube or a tube having a surface that contacts said natriuretic peptide that is coated with silicone.

2. The method of claim 1, wherein the sample does not contain any protease inhibitor.

3. The method of claim 1, wherein the sample does not contain aprotinin.

4. A method for measuring an amount of a natriuretic peptide in a blood sample at the time of collection of said sample comprising
   i) allowing the blood sample to stand at a temperature of 4° C. to room temperature for a period of time longer than 6 hours in a plastic tube or in a tube having a surface that contacts the natriuretic peptide that is coated with silicone, and
   ii) measuring by a standard method the amount of the natriuretic peptide in said blood sample that has stood for a period of time.

5. The method of claim 4, in which the sample has stood for at least 24 hours.

6. The method of claim 4, in which the sample is allowed to stand at room temperature.

7. The method of claim 5, in which the sample is allowed to stand at room temperature.

8. The method of claim 4, wherein the sample does not contain a protease inhibitor.

9. The method of claim 4, wherein the sample does not contain aprotinin.

10. The method of claim 5, wherein the sample does not contain a protease inhibitor.

11. The method of claim 5, wherein the sample does not contain aprotinin.

12. The method of claim 6, wherein the sample does not contain a protease inhibitor.

13. The method of claim 6, wherein the sample does not contain aprotinin.

14. The method of claim 7, wherein the sample does not contain a protease inhibitor.

15. The method of claim 7, wherein the sample does not contain aprotinin.

16. The method of claim 4, in which the activity of the natriuretic peptide measured after the period of standing is at least 80% of the activity of the natriuretic peptide at the time of collection.

17. The method of claim 14, in which the activity of the natriuretic peptide measured after the period of standing is at least 80% of the activity of the natriuretic peptide at the time of collection.

18. The method of claim 15, in which the activity of the natriuretic peptide measured after the period of standing is at least 80% of the activity of the natriuretic peptide at the time of collection.

* * * * *